United States Patent
Crone et al.

(10) Patent No.: US 7,435,860 B2
(45) Date of Patent: Oct. 14, 2008

(54) METHOD FOR THE PRODUCTION OF BUTADINE FROM N-BUTANE

(75) Inventors: Sven Crone, Limburgerhof (DE);
Catharina Klanner, Mannheim (DE);
Götz-Peter Schindler, Mannheim (DE);
Mark Duda, Ludwigshafen (DE);
Frieder Borgmeier, Mannhein (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/721,240

(22) PCT Filed: Dec. 7, 2005

(86) PCT No.: PCT/EP2005/013105

§ 371 (c)(1),
(2), (4) Date: Jun. 8, 2007

(87) PCT Pub. No.: WO2006/061202

PCT Pub. Date: Jun. 15, 2006

(65) Prior Publication Data

US 2008/0097133 A1   Apr. 24, 2008

(30) Foreign Application Priority Data

Dec. 9, 2004  (DE) .................. 10 2004 059 356

(51) Int. Cl.
*C07C 5/333*  (2006.01)

(52) U.S. Cl. .................. 585/325; 585/616; 585/621; 585/628; 585/629

(58) Field of Classification Search .................. 585/325, 585/616, 621, 628, 629
See application file for complete search history.

(56) References Cited

U.S. PATENT DOCUMENTS 4,504,692 A * 3/1985 Arakawa et al. ............. 585/633
2005/0171311 A1   8/2005 Schindler et al.

FOREIGN PATENT DOCUMENTS

WO   WO-2004/007408   1/2004

* cited by examiner

*Primary Examiner*—Thuan Dinh Dang
(74) *Attorney, Agent, or Firm*—Connolly Bove Lodge & Hutz LLP

(57) ABSTRACT

A process for preparing butadiene, comprising nonoxidatively dehydrogenating n-butane from a stream (a) in a first dehydrogenation zone to obtain stream (b) comprising 1-butene and 2-butene; oxidatively dehydrogenating the 1-butene and 2-butene of (b) in the presence of an oxygenous gas in a second dehydrogenation zone to obtain stream (c) comprising n-butane, butadiene, hydrogen, carbon dioxide, and steam; compressing and cooling (c) to obtain stream (d2) comprising n-butane, butadiene, hydrogen, carbon dioxide, and steam; extractively distilling (d2) into stream (e1) comprising butadiene and stream (e2) comprising n-butane, hydrogen, carbon dioxide, and steam; compressing and cooling (e2) to obtain stream (f1) comprising n-butane and water and stream (f2) comprising n-butane, hydrogen, and carbon dioxide; cooling (f2) to obtain stream (g1) comprising n-butane and stream (g2) comprising carbon dioxide and hydrogen; phase separating water from (f1) to obtain stream (h1) comprising n-butane; and recycling (h1) into the first dehydrogenation zone.

6 Claims, 1 Drawing Sheet

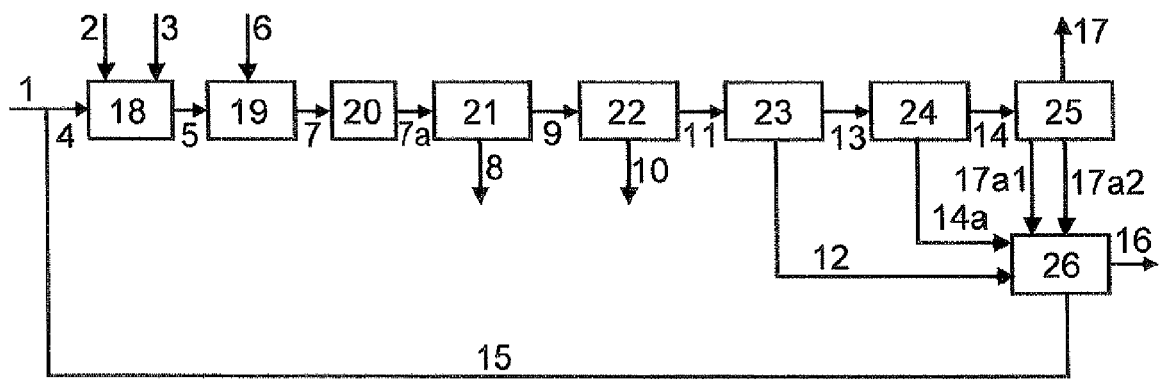

METHOD FOR THE PRODUCTION OF BUTADINE FROM N-BUTANE

RELATED APPLICATIONS

This application is a national stage application (under 35 U.S.C. § 371) of PCT/EP2005/013105 filed Dec. 7, 2005, which claims benefit of German application 10 2004 059 356.6 filed Dec. 9, 2004.

The invention relates to a process for preparing butadiene from n-butane.

Butadiene is an important basic chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to styrene.

Butadiene can be prepared by thermally cracking (steamcracking) saturated hydrocarbons, in which case naphtha is typically used as the raw material. In the steamcracking of naphtha, a hydrocarbon mixture of methane, ethane, ethene, acetylene, propane, propene, propyne, allene, butenes, butadiene, butynes, methylailene, $C_6$ and higher hydrocarbons is obtained.

A disadvantage of the generation of butadiene in a cracking process is that larger amounts of undesired coproducts are inevitably obtained.

It is an object of the invention to provide a process for preparing butadiene from n-butane, in which coproducts are obtained to a minimal extent.

BRIEF DESCRIPTION OF THE DRAWING

The FIGURE schematically illustrates the steps of the process described in the Example.

The object is achieved by a process for preparing butadiene from n-butane, comprising the steps of A) providing a feed gas stream a comprising n-butane;

B) feeding the feed gas stream a comprising n-butane into at least one first dehydrogenation zone and nonoxidatively, catalytically dehydrogenating n-butane to obtain a gas stream b comprising n-butane, 1-butene, 2-butene, butadiene and hydrogen, with or without carbon dioxide and with or without steam;

C) feeding the gas stream b and an oxygenous gas into at least one second dehydrogenation zone and oxidatively dehydrogenating 1-butene and 2-butene to obtain a gas stream c comprising n-butane, butadiene, hydrogen, carbon dioxide and steam, D) compressing in at least one first compression stage and cooling the gas stream c to obtain at least one condensate stream d1 comprising water and a gas stream d2 comprising n-butane, butadiene, hydrogen, carbon dioxide and steam, E) separating the gas stream d2 by extractive distillation into a product stream e1 consisting substantially of butadiene and a stream e2 comprising n-butane, hydrogen, carbon dioxide and steam, F) compressing in at least one further compression stage and cooling the gas stream e2 to obtain at least one condensate stream f1 comprising n-butane and water, and a gas stream f2 comprising n-butane, hydrogen and carbon dioxide, G) cooling the gas stream f2 to obtain a condensate stream g1 comprising n-butane and an offgas stream g2 comprising carbon dioxide and hydrogen, H) removing water from the at least one condensate stream f1 and, if appropriate, from the condensate stream g1 by phase separation to obtain at least one recycle stream h1 comprising n-butane and at least one wastewater stream h2, and recycling the at least one recycle stream h1 into the first dehydrogenation zone.

The process according to the invention is notable for particularly effective utilization of the raw materials. Thus, losses of the n-butane raw material are minimized by recycling unconverted n-butane into the dehydrogenation. The coupling of nonoxidative catalytic dehydrogenation and oxidative dehydrogenation achieves a high butadiene yield. Compared to the generation of butadiene by cracking, the process is notable for high selectivity. No coproducts are obtained. The complicated removal of butadiene from the product gas mixture of the cracking process is dispensed with.

In a first process part, A, a feed gas stream a comprising n-butane is provided. Typically, the starting raw materials are n-butane-rich gas mixtures such as liquefied petroleum gas (LPG). LPG comprises substantially saturated $C_2$-$C_5$ hydrocarbons. In addition, it also comprises methane and traces of $C_6^+$ hydrocarbons. The composition of LPG can vary markedly. Advantageously, the LPG used contains at least 10% by weight of butanes.

Alternatively, a refined $C_4$ stream from crackers or refineries may be used.

In one variant of the process according to the invention, the provision of the dehydrogenation feed gas stream comprising n-butane comprises the steps of (A1) providing a liquefied petroleum gas (LPG) stream, (A2) removing propane and any methane, ethane and $C_5^+$ hydrocarbons (mainly pentanes, additionally hexanes, heptanes, benzene, toluene) from the LPG stream to obtain a stream comprising butanes (n-butane and isobutane), (A3) removing isobutane from the stream comprising butanes to obtain the feed gas stream comprising n-butane, and, if desired, isomerizing the isobutane removed to give an n-butane/isobutane mixture and recycling the n-butane/isobutane mixture into the isobutane removal.

Propane and any methane, ethane and $C_5^+$ hydrocarbons are removed, for example, in one or more customary rectification columns. For example, in a first column, low boilers (methane, ethane, propane) may be removed overhead, and, in a second column, high boilers ($C_5^+$ hydrocarbons) may be removed at the bottom of the column. A stream comprising butanes (n-butane and isobutane) is obtained, from which isobutane is removed, for example in a customary rectification column. The remaining stream comprising n-butane is used as the feed gas stream for the downstream butane dehydrogenation.

The isobutane stream removed can be subjected to an isomerization. To this end, the stream comprising isobutane is fed into an isomerization reactor. The isomerization of isobutane to n-butane may be carried out as described in GB-A 2 018 815. An n-butane/isobutane mixture is obtained and is fed into the n-butane/isobutane separating column.

The isobutane stream removed may also be sent to a further use, for example for preparing methacrylic acid, polyisobutene or methyl tert-butyl ether.

The feed gas stream a, comprising n-butane, comprises generally at least 60% by weight of n-butane, preferably at least 90% by weight of n-butane. In addition, it may also comprise $C_1$-$C_6$ hydrocarbons as secondary constituents.

In one process part, B, the feed gas stream comprising n-butane is fed into a dehydrogenation zone and subjected to a nonoxidative catalytic dehydrogenation. In this dehydrogenation, n-butane is partly dehydrogenated in a dehydrogenation reactor over a dehydrogenating catalyst to give 1-butene and 2-butene, and butadiene is also formed. In addition, hydrogen and small amounts of low boilers (methane, ethane, ethene, propane and propene) are obtained. Depending on the method of the dehydrogenation, $CO_2$, water and nitrogen may also be present in the product gas mixture of the nonoxidative catalytic n-butane dehydrogenation. Unconverted n-butane is additionally present in the product gas mixture.

The nonoxidative catalytic n-butane dehydrogenation may be carried out with or without oxygenous gas as a cofeed. It is preferably carried out as an autothermal nonoxidative catalytic dehydrogenation with feeding of oxygen as a cofeed. In the autothermal method, the heat required is generated directly in the reactor system by combustion of hydrogen and/or hydrocarbons in the presence of oxygen. If appropriate, a cofeed comprising hydrogen may additionally be admixed. Oxygen may also be fed in as pure oxygen or as oxygenous gas, for example as air. In order to restrict the inert gas fraction, oxygen may be fed in as oxygen-rich gas, generally having an oxygen content of at least 75% by volume, preferably at least 90% by volume. A suitable oxygenous gas is oxygen of technical grade purity, having an oxygen content of approx. 99% by volume, As a result of the use of an oxygenous cofeed with a high oxygen content only small amounts of inert gases (nitrogen) are introduced into the overall process. This has an advantageous effect in the subsequent workup, since the losses of $C_4$ hydrocarbons which are discharged with the inert gases are lower.

One feature of the nonoxidative method compared to an oxidative method is that free hydrogen is not formed in the oxidative dehydrogenation.

The nonoxidative catalytic n-butane dehydrogenation may in principle be carried out in any reactor types and methods disclosed by the prior art. A comparatively comprehensive description of dehydrogenation processes suitable in accordance with the invention is also contained in "Catalytica® Studies Division, Oxidative Dehydrogenation and Alternative Dehydrogenation Processes" (Study Number 4192OD, 1993, 430 Ferguson Drive, Mountain View, Calif., 94043-5272, USA).

A suitable reactor form is a fixed bed tubular or tube bundle reactor. In these reactors, the catalyst (dehydrogenation catalyst and, when working with oxygen as the cofeed, optionally a specialized oxidation catalyst) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a small steam dilution is used (analogously to the Linde process for propane dehydrogenation), or else from 3 to 8 bar when a high steam dilution is used (analogously to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical gas hourly space velocities (GHSV) are from 500 to 2000 $h^{-1}$, based on the hydrocarbon used. The catalyst geometry may, for example, be spherical or cylindrical (hollow or solid).

The nonoxidative catalytic n-butane dehydrogenation may also be carried out under heterogeneous catalysis in a fluidized bed, as described in Chem. Eng. Sci. 1992 b, 47 (9-11) 2313. Appropriately, two fluidized beds are operated in parallel, of which one is generally in the state of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature. The admixing of a cofeed comprising oxygen allows the preheater to be dispensed with and the required heat to be generated directly in the reactor system by combustion of hydrogen and/or hydrocarbons in the presence of oxygen. If appropriate, a hydrogen-containing cofeed may additionally be admixed.

The nonoxidative catalytic n-butane dehydrogenation may be carried out in a tray reactor with or without oxygenous gas as a cofeed. It is preferably carried out with oxygenous gas as a cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated with a fixed catalyst bed. In the simplest case, the fixed catalyst beds are disposed axially in a shaft furnace reactor or in the annular gaps of concentric cylindrical grids. A shaft furnace reactor corresponds to one tray. The performance of the dehydrogenation in a single shaft furnace reactor corresponds to a preferred embodiment, in which it is possible to work with oxygenous cofeed. In a further preferred embodiment, the dehydrogenation is carried out in a tray reactor having 3 catalyst beds. In a method without oxygenous gas as cofeed, the reaction gas mixture is subjected to intermediate heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partially combusted, which generates directly in the reaction gas mixture at least a portion of the heat required for dehydrogenation in the at least one reaction zone.

In general, the amount of oxygenous gas added to the reaction gas mixture is selected in such a way that the amount of heat required for the dehydrogenation of n-butane is generated by the combustion of the hydrogen present in the reaction gas mixture and of any hydrocarbons present in the reaction gas mixture and/or of carbon present in the form of coke. In general, the total amount of oxygen supplied, based on the total amount of butane, is from 0.001 to 0.5 mol/mol, preferably from 0.005 to 0.2 mol/mol, more preferably from 0.05 to 0.2 mol/mol. Oxygen may be used either as pure oxygen or as an oxygenous gas in a mixture with inert gases, for example in the form of air. The oxygenous gas comprises preferably at least 70% by volume, more preferably at least 95% by volume, of oxygen, in order to minimize the inert gas fraction in the product gas stream of the autothermal dehydrogenation. The inert gases and the resulting combustion gases, though, have an additional diluting action and thus promote the heterogeneously catalyzed dehydrogenation.

The hydrogen combusted to generate heat is the hydrogen formed in the catalytic n-butane dehydrogenation and also any hydrogen additionally added to the reaction gas mixture as hydrogenous gas. The amount of hydrogen present should preferably be such that the molar $H_2/O_2$ ratio in the reaction gas mixture immediately after the oxygen has been fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. One embodiment works in the presence of one or more oxidation catalysts which selectively catalyze the combustion of hydrogen with oxygen in the presence of hydrocarbons. The combustion of these hydrocarbons with oxygen to give $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one or in more than one reaction zone, or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and, if appropriate, of hydrogenous gas upstream of every tray of a tray reactor. In a further embodiment of the process according to the invention, oxygenous gas and, if appropriate, hydrogenous gas are fed in upstream of every tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C.; the pressure in the last catalyst bed of the tray reactor is generally from 0.2 to 5 bar, preferably from 1 to 3 bar. The GHSV is generally from 500 to 2000 $h^{-1}$, and in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates or germanium, tin, lead, arsenic, antimony and bismuth. A further preferred catalyst which catalyzes the combustion of hydrogen comprises a noble metal of transition group VII and/or I of the periodic table.

The dehydrogenation catalysts used generally comprise a support and an active composition. The support generally consists of a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide, and particular preference is given to mixtures of zirconium dioxide and silicon dioxide.

The active compositions of the dehydrogenation catalysts generally comprise one or more elements of transition group VII of the periodic table, preferably platinum and/or palladium, more preferably platinum. Furthermore, the dehydrogenation catalysts may comprise one or more elements of main group I and/or II, preferably potassium and/or cesium. The dehydrogenation catalysts may further comprise one or more elements of transition group III including the lanthanides and actinides, preferably lanthanum and/or cerium. Finally, the dehydrogenation catalysts may comprise one or more elements of main group III and/or IV, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all dehydrogenation catalysts which are disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used in accordance with the invention. Particularly preferred catalysts for the above-described variants of the autothermal n-butane dehydrogenation are the catalysts according to examples 1, 2, 3 and 4 of DE-A 199 37 107.

Preference is given to carrying out the n-butane dehydrogenation in the presence of steam. The added steam serves as a heat carrier and supports the gasification of organic deposits on the catalysts, which counteracts carbonization of the catalysts and increases the lifetime of the catalysts. The organic deposits are converted to carbon monoxide, carbon dioxide and in some cases water.

The dehydrogenation catalyst may be regenerated in a manner known per se. For instance, steam may be added to the reaction gas mixture or a gas comprising oxygen may be passed from time to time over the catalyst bed at elevated temperature and the deposited carbon burnt off. Dilution with steam shifts the equilibrium toward the products of dehydrogenation. After the regeneration, the catalyst is, if appropriate, reduced with a hydrogenous gas.

The nonoxidative catalytic n-butane dehydrogenation affords a gas mixture which, in addition to butadiene, 1-butene, 2-butene and unconverted n-butane, comprises secondary constituents. Customary secondary constituents are hydrogen, steam, nitrogen, CO and $CO_2$, methane, ethane, ethene, propane and propene. The composition of the gas mixture leaving the first dehydrogenation zone can vary greatly depending on the method of dehydrogenation. For instance, when the preferred autothermal dehydrogenation with feeding of oxygen and additional hydrogen is carried out, the product gas mixture comprises a comparatively high content of steam and carbon oxides. In methods without feeding of oxygen, the product gas mixture of the nonoxidative dehydrogenation has a comparatively high content of hydrogen.

The product gas stream of the nonoxidative autothermal n-butane dehydrogenation typically contains from 0.1 to 15% by volume of butadiene, from 1 to 20% by volume of 1-butene, from 1 to 40% by volume of 2-butene (cis/trans-2-butene), from 20 to 70% by volume of n-butane, from 1 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen and from 0 to 10% by volume of carbon dioxide.

The product gas stream b leaving the first dehydrogenation zone can be separated into two substreams, in which case only one of the two substreams is subjected to the further process parts C to H and the second substream is recycled into the first dehydrogenation zone. An appropriate procedure is described in DE-A 102 11 275. However, it is also possible to subject the entire product gas stream b of the nonoxidative catalytic n-butane dehydrogenation to the further process parts C to H.

According to the invention, the nonoxidative catalytic dehydrogenation is followed downstream by an oxidative dehydrogenation (oxydehydrogenation) as process part C. This essentially dehydrogenates 1-butene and 2-butene to 1,3-butadiene, and 1-butene is generally virtually fully depleted.

This may in principle be carried out in all reactor types and methods known from the prior art, for example in a fluidized bed, in a tray furnace, in a fixed bed tubular or tube bundle reactor, or in a plate heat exchanger reactor. To carry out the oxidative dehydrogenation, a gas mixture is required which has a molar oxygen:n-butenes ratio of at least 0.5. Preference is given to working at an oxygen:n-butenes ratio of from 0.55 to 50. To attain this value, the product gas mixture stemming from the nonoxidative catalytic dehydrogenation is mixed with pure oxygen or an oxygenous gas. In the case of the first (autothermal) dehydrogenation stage B), the oxygenous gas may be air or comprise predominantly oxygen, generally at least 70% by volume, preferably at least 95% by volume, in order to minimize the inert gas fraction in the product gas stream of the oxydehydrogenation. Preference is given to oxygen of technical-grade purity. This typically comprises at least 99% by volume of oxygen. The resulting oxygenous gas mixture is then sent to the oxydehydrogenation.

The catalysts which are particularly suitable for the oxydehydrogenation are generally based on an Mo—Bi—O multimetal oxide system which generally additionally comprises iron. In general, the catalyst system also comprises additional components from groups 1 to 15 of the periodic table, for example potassium, magnesium, zirconium, chromium, nickel, cobalt, cadmium, tin, lead, germanium, lanthanum, manganese, tungsten, phosphorus, cerium, aluminum or silicon.

Suitable catalysts and their preparation are described, for example, in U.S. Pat. No. 4,423,281 ($Mo_{12}BiNi_8Pb_{0.5}Cr_3K_{0.2}O$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3PO_{0.5}Mg_{7.5}K_{0.1}O_x$+$SiO_2$) and DE-A 24 40 329 ($Mo_{12}BiCO_{4.5}Ni_{2.5}Cr_3P_{0.5}K_{0.1}O_x$).

The stoichiometry of the active composition of a multitude of multimetal oxide catalysts suitable for the oxydehydrogenation can be encompassed under the general formula (I)

$$Mo_{12}Bi_aFe_bCo_cNi_dCr_eX^1_fK_gO_x \qquad (I)$$

in which the variables are each defined as follows:

| | |
|---|---|
| $X^1$ = | W, Sn, Mn, La, Ce, Ge, Ti, Zr, Hf, Nb, P, Si, Sb, Al, Cd and/or Mg; |
| a = | from 0.5 to 5, preferably from 0.5 to 2; |
| b = | from 0 to 5, preferably from 2 to 4; |
| c = | from 0 to 10, preferably from 3 to 10; |
| d = | from 0 to 10; |
| e = | from 0 to lot preferably from 0.1 to 4; |
| f = | from 0 to 5, preferably from 0.1 to 2; |
| g = | from 0 to 2, preferably from 0.01 to 1; and |
| x = | a number which is determined by the valency and frequency of the elements in (I) other than oxygen. |

In the process according to the invention, preference is given to using an Mo—Bi—Fe—O multimetal oxide system for the oxydehydrogenation, particular preference being given to an Mo—Bi—Fe—Cr—O or Mo—Bi—Fe—Zr—O multimetal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$) U.S. Pat. No. 4,424,141 ($Mo_{12}BiFe_3CO_{4.5}Ni_{2.5}P_{0.5}K_{0.1}O_x$+$SiO_2$), DE-A 25 30 959 ($Mo_{12}BiFe_3CO_{4.5}Ni_{2.5}Cr_{0.5}K_{0.1}O_x$, $Mo_{13.75}BiFe_3CO_{4.5}Ni_{2.5}Ge_{0.5}K_{0.8}O_x$, $Mo_{12}BiFe_3CO_{4.5}Ni_{2.5}Mn_{0.5}K_{0.1}O_x$ and $Mo_{12}BiFe_3CO_{4.5}Ni_{2.5}La_{0.5}K_{0.1}O_x$), U.S. Pat. No. 3,911,039 ($Mo_{12}BiFe_3CO_{4.5}Ni_{2.5}Sn_{0.5}K_{0.1}O_x$), DE-A 25 30 959 and DE-A 24 47 825 ($Mo_{12}BiFe_3CO_{4.5}Ni_{2.5}W_{0.5}K_{0.1}O_x$). The preparation and characterization of the catalysts mentioned are described comprehensively in the documents cited.

The oxydehydrogenation catalyst is generally used in the form of shaped bodies having an average size of over 2 mm. Owing to the pressure drop to be observed when the process is performed, smaller shaped bodies are generally unsuitable. Examples of suitable shaped bodies include tablets, cylinders, hollow cylinders, rings, spheres, strands, wagon wheels or extrudates. Special shapes, for example "trilobes" and "tristars" (see EP-A-0 593 646) or shaped bodies having at least one notch on the exterior (see U.S. Pat. No. 5,168,090) are likewise possible.

In general, the catalyst used may be used in the form of an unsupported catalyst. In this case, the entire shaped catalyst body consists of the active composition, including any auxiliaries, such as graphite or pore formers, and also further components. In particular, it has been found to be advantageous to use the Mo—Bi—Fe—O catalyst used with preference for the oxydehydrogenation of the n-butenes to butadiene in the form of an unsupported catalyst. Furthermore, it is possible to apply the active compositions of the catalysts to a support, for example an inorganic, oxidic shaped body. Such catalysts are generally referred to as coated catalysts.

The oxydehydrogenation is generally carried out at a temperature of from 220 to 490° C. and preferably from 250 to 450° C. A reactor inlet pressure is selected which is sufficient to overcome the flow resistances in the plant and the subsequent workup. This reactor inlet pressure is generally from 0.005 to 1 MPa gauge, preferably from 0.01 to 0.5 MPa gauge. By its nature, the gas pressure applied in the inlet region of the reactor decreases substantially over the entire catalyst bed.

The coupling of the nonoxidative catalytic, preferably autothermal, dehydrogenation with the oxidative dehydrogenation of the n-butenes formed affords a very much higher yield of butadiene based on n-butane used. The nonoxidative dehydrogenation can also be operated in a gentler manner. Comparable butadiene yields would only be achievable with an exclusively nonoxidative dehydrogenation at the cost of distinctly reduced selectivities. An exclusively oxidative dehydrogenation only achieves low n-butane conversions.

In addition to butadiene and unconverted n-butane, the product gas stream c leaving the oxidative dehydrogenation also comprises hydrogen, carbon dioxide and steam. As secondary constituents, it can also comprise oxygen, nitrogen, methane, ethane, ethene, propane and propene, and also oxygenous hydrocarbons, known as oxygenates. In general, it comprises virtually no 1-butene and only small fractions of 2-butene.

In general, the product gas stream c leaving the oxidative dehydrogenation has from 1 to 40% by volume of butadiene, from 1 to 80% by volume of n-butane, from 0 to 5% by volume of 2-butene, from 0 to 1% by volume of 1-butene, from 5 to 70% by volume of steam, from 0 to 10% by volume of low-boiling hydrocarbons (methane, ethane, ethene, propane and propene), from 0.1 to 15% by volume of hydrogen, from 0 to 40% by volume of nitrogen, from 0 to 10% by volume of carbon dioxide and from 0 to 10% by volume of oxygenates. Oxygenates may, for example, be furan, acetic acid, maleic anhydride, maleic acid, propionic acid, acetaldehyde, acrolein, formaldehyde, formic acid and butyraldehyde. In addition, traces of acetylene, propyne and 1,2-butadiene may also be present.

The product gas stream c may also comprise small amounts of oxygen. When the product gas stream c contains more than just minor traces of oxygen, a process stage is generally carried out to remove residual oxygen from the product gas stream c. The residual oxygen may have a troublesome effect insofar as it can act as an initiator for polymerization reactions in downstream process steps. This is a risk especially in the course of the distillative removal of butadiene (step E)) and can lead there to deposits of polymers (formation of "popcorn") in the extractive distillation column. Preference is given to carrying out the oxygen removal immediately after the oxidative dehydrogenation. To this end, a catalytic combustion stage is generally carried out in which oxygen is reacted with the hydrogen present in the gas stream c in the presence of a catalyst. This achieves a reduction in the oxygen content down to small traces.

A suitable catalyst for the oxidation of hydrogen comprises, supported on α-alumina, from 0.01 to 0.1% by weight of platinum and from 0.01 to 0.1% by weight of tin, based on the total weight of the catalyst. Platinum and tin are used advantageously in a weight ratio of from 1:4 to 1:0.2, preferably in a ratio of from 1:2 to 1:0.5, in particular in a ratio of approximately 1:1. Advantageously, the catalyst comprises from 0.05 to 0.09% by weight of platinum and from 0.05 to 0.09% by weight of tin, based on the total weight of the catalyst. In addition to platinum and tin, alkali metal and/or alkaline earth metal compounds may if appropriate be used in amounts of less than 2% by weight, in particular less than 0.5% by weight. More preferably, the alumina catalyst comprises exclusively platinum and tin. The catalyst support of α-alumina advantageously has a BET surface area of from 0.5 to 15 m$^2$/g, preferably from 2 to 14 m$^2$/g, in particular from 7 to 11 m$^2$/g. The support used is preferably a shaped body. Preferred geometries are, for example, tablets, annular tablets, spheres, cylinders, star extrudates or toothed wheel-shaped extrudates having diameters of from 1 to 10 mm, preferably from 2 to 6 mm. Particular preference is given to spheres or cylinders, in particular cylinders.

Alternative processes for removing residual oxygen from the product gas stream c comprise the contacting of the product gas stream with a mixture of metal oxides which comprise copper in reduced form in the 0 oxidation state. In addition, such a mixture generally also comprises aluminum oxides and zinc oxides, the copper content being typically up to 10% by weight. In this way, virtually full conversion of residual oxygen is possible. In addition, further methods of removing oxygen traces may be used. Examples are the removal by means of molecular sieves or use of membranes.

In one process stage, D), the gas stream c is compressed in at least one first compression stage and subsequently cooled, in the course of which at least one condensate stream d1 comprising water condenses out and the gas stream d2 comprising n-butane, butadiene, hydrogen, carbon dioxide and steam remains.

Preferably, the gas stream c is cooled to a temperature in the range from 15 to 60° C. before the first compression stage. Cooling is carried out via direct or indirect heat exchange. For direct heat exchange, recycled condensate is brought into contact with gas stream c. Suitable contact apparatuses are wash columns, quench columns, venturi washers. Optionally, NaNO$_2$ is added to the quench cycle stream to remove traces of oxygen. Optionally, stabilizer against the formation of popcorn, polymers or butadiene epoxides is added to the quench cycle stream.

The compression may be effected in one or more stages. Overall, compression is effected from a pressure in the range from 1.0 to 4.0 bar to a pressure in the range from 3.5 to 8.0 bar. Each compression stage is followed by a cooling stage in which the gas stream is cooled to a temperature in the range from 15 to 60° C. The condensate stream d1 may thus also comprise a plurality of streams in the case of multistage compression.

The gas stream d2 consists generally substantially of C$_4$ hydrocarbons (substantially n-butane and butadiene), hydrogen, carbon dioxide and steam. In addition, the stream d2 may also comprise low boilers and inert gases (nitrogen) as further secondary components. The wastewater stream d1 consists generally to an extent of at least 80% by weight, preferably to an extent of at least 90% by weight, of water and comprises additionally, to a small extent, low boilers, C$_4$ hydrocarbons, oxygenates and carbon dioxide.

Suitable compressors are, for example, turbo compressors and piston compressors including rotary piston compressors. The compressors may be driven, for example, by an electric motor, an expander or a gas or steam turbine. Typical compression ratios (outlet pressure:inlet pressure) for a compressor stage, depending on the design, are between 1.5 and 3.0.

The compressed gas is cooled by heat exchangers which may be designed, for example, as tube bundle, spiral or plate heat exchangers. The coolants used in the heat exchangers are cooling water or heat carrier oils. In addition, preference is given to using air cooling with use of fans.

In one process stage, E), the gas stream d2 is separated by extractive distillation into a product stream e1 consisting substantially of butadiene and a stream e2 comprising n-butane, hydrogen, carbon dioxide and steam.

The extractive distillation may be carried out, for example, as described in Erdöl und Kohle—Erdgas—Petrochemie [Mineral Oil and Coal—Natural Gas—Petrochemistry] volume 34 (8), pages 343-346 or Ullmanns Enzyklopädie der Technischen Chemie, volume 9, 4th edition 1975, pages 1 to 18.

To this end, the gas stream d2 is contacted in an extraction zone with an extractant, preferably an N-methylpyrrolidone (NMP)/water mixture. The extraction zone is generally configured in the form of a wash column which comprises trays, random packings or structured packings as internals. It generally has from 30 to 70 theoretical plates, so that sufficiently good separating action is achieved. The wash column preferably has a backwash zone in the top of the column. This backwash zone serves to recycle the extractant present in the gas phase by means of a liquid hydrocarbon reflux, for which the top fraction is condensed beforehand. Typical temperatures at the top of the column are between 30 and 60° C. The mass ratio of extractant to $C_4$ product gas stream d2 in the feed of the extraction zone is generally from 10:1 to 20:1.

Suitable extractants are butyrolactone, nitrites such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In general, alkyl-substituted lower aliphatic amides or N-alkyl-substituted cyclic amides are used. Particularly advantageous are dimethylformamide, acetonitrile, furfural and especially NMP.

However, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. Particularly suitable is NMP, preferably in aqueous solution, preferably with from 0 to 20% by weight of water, more preferably with from 7 to 10% by weight of water, in particular with 8.3% by weight of water.

In the extractive distillation column, a gaseous stream e2 comprising n-butane, steam, hydrogen and carbon dioxide is obtained, which is generally drawn off via the top of the column, and the side draw stream obtained is a mixture of extractant and butadiene. From this mixture, butadiene may be obtained subsequently as a pure product. The extractant which also comprises butadiene and any secondary components (impurities) is obtained as a side draw stream. The side draw stream is, if appropriate after carrying out further purification steps, recycled back into the extractive distillation.

The stream e2 may comprise, as further constituents, also butenes, low boilers and inert gases (nitrogen).

For example, the extractive distillation, isolation of the pure butadiene and purification of the extractant may be carried out as follows: the side draw stream of the extractive distillation column, composed of extractant and butadiene which still comprises impurities (acetylene, propyne, 1,2-butadiene), is fed into a wash column which is charged with fresh extractant. At the top of the wash column, crude butadiene which comprises, for example, 98% by weight of butadiene is drawn off. The bottom draw stream is enriched with acetylene and is recycled into the extractive distillation. The crude butadiene may comprise propyne and 1,2-butadiene as impurities. To remove these impurities, the crude butadiene is fed to a first purifying distillation column and a propyne-enriched butadiene stream is removed overhead. The bottom draw stream which is substantially propyne-free, but still contains traces of 1,2-butadiene, is fed into a second purifying distillation column in which a substantially 1,2-butadiene-free pure butadiene stream having a purity of, for example, at least 99.6% by weight as a top draw stream or side draw stream in the rectifying section of the column, and a 1,2-butadiene-enriched bottom draw stream, are obtained.

To purify the extractant, a portion of the extractant is discharged from the extractive distillation column as a bottom draw stream and regenerated as follows: the extraction solution is transferred into a desorption zone with reduced pressure and/or elevated temperature compared to the extraction zone, and butadiene and acetylene traces present are desorbed from the extraction solution. The desorption zone may be designed, for example, in the form of a wash column which has from 5 to 15, preferably from 8 to 10, theoretical plates and a backwash zone having, for example, 4 theoretical plates. This backwash zone serves to recover the extractant present in the gas phase by means of liquid hydrocarbon reflux, for which the top fraction is condensed beforehand. The internals provided are structured packings, trays or random packings. The pressure added to the top of the column is, for example, 1.5 bar. The temperature in the bottom of the column is, for example, from 130 to 150° C. At the bottom of the column, a substantially acetylene-free extractant is obtained and is recycled into the extractive distillation column.

The product-of-value stream e1, as is obtained, for example, at the top draw stream of the second purifying distillation column, may comprise up to 100% by volume of butadiene.

The extraction solution is transferred into a desorption zone having reduced pressure and/or elevated temperature compared to the extraction zone, and the butadiene is desorbed from the extraction solution. The desorption zone may be designed, for example, in the form of a wash column which has from 5 to 15, preferably from 8 to 10, theoretical plates, and a backwash zone having, for example, 4 theoretical plates. This backwash zone serves to recover the extractant present in the gas phase by means of liquid hydrocarbon reflux, for which the top fraction is condensed beforehand. The internals provided are structured packings, trays or random packings. The pressure at the top of the column is, for example, 1.5 bar. The temperature in the bottom of the column is, for example, from 130 to 150° C.

In one process stage, F), the gas stream e2 is compressed in at least one further compression stage and subsequently cooled to obtain at least one condensate stream f1 comprising n-butane and water, a gas stream f2 comprising n-butane, hydrogen and carbon dioxide.

The compression may again be effected in one or more stages. In general, compression is effected from a pressure in the range from 3.5 to 8 bar to a pressure in the range from 12 to 40 bar. Each compression stage is followed by a cooling stage in which the gas stream is cooled to a temperature in the range from 15 to 60° C. The condensate stream f1 may thus also comprise a plurality of streams in the case of multistage compression.

Preference is given to carrying out the compression in two stages, compression being effected in a first compression stage to a pressure of from 8 to 15 bar and in a second compression stage to a pressure of from 12 to 40 bar. After each compression stage there is a cooling stage (intermediate cooling), in each case to obtain one condensate stream. These are fed together or separately to the phase separation.

The gas stream f2 comprises generally n-butane, carbon dioxide and hydrogen as the essential components. In addition, it may also comprise butenes, low boilers and inert gases (nitrogen) as further secondary components. Steam may also be present in small amounts. The condensate stream f1 consists generally to an extent of at least 40% by weight, preferably to an extent of at least 60% by weight, of $C_4$ hydrocarbons (substantially n-butane, additionally in some cases also butenes) and comprises additionally water and generally carbon dioxide; it may further comprise low boilers and oxygenates.

In one process stage, G), the gas stream f2 is cooled to obtain a condensate stream g1 comprising n-butane and an offgas stream g2 comprising carbon dioxide and hydrogen. The condensation may be carried out in more than one stage, for example in two stages or as rectification with 5 to 15 theoretical stages. In this case, a plurality of condensate streams g1 may be obtained.

Before the condensation stage G) is carried out, small amounts of steam may be removed from the gas stream f2 by absorption on a molecular sieve. This is necessary at condensation temperatures of ≦0° C. in order to avoid the freezing out of water.

The condensate stream g1 may, for example, be condensed in surface condensers. In these condensers, the gas stream f2 comes into contact with tubes which are flowed through by cooling medium. Useful coolants are, for example, water, air and cooling brine. Injection condensers in which the coolant, preferably water, is injected directly into the gas stream which comprises the components to be condensed are also possible.

In general, the gas stream f2 is cooled to a temperature in the range from −30 to +20° C. The condensate stream g1 comprises predominantly $C_4$ hydrocarbons (substantially n-butane and in some cases butenes), generally to an extent of at least 50% by weight, preferably to an extent of at least 70% by weight, and generally additionally comprises carbon dioxide. In addition, it may also comprise low boilers and small amounts of water.

In one process step, H), water is removed by phase separation from the at least one condensate stream f1 and, if appropriate, the condensate stream g1, to obtain at least one recycle stream h1 comprising n-butane and at least one wastewater stream h2, and the at least one recycle stream h1 is recycled into the first dehydrogenation zone.

To this end, the condensate streams f1 and, if appropriate, g1 are fed separately or combined to one or more phase separation apparatuses. The condensate stream g1 is subjected to a phase separation if it still has a significant water content, otherwise it can be recycled directly into the first dehydrogenation zone. A combined $C_4$ hydrocarbon stream h1 or a plurality of separate $C_4$ hydrocarbon streams h1 is/are obtained. The hydrocarbon stream(s) h1 comprise(s) predominantly $C_4$ hydrocarbons (substantially n-butane, additionally in some cases butenes), generally to an extent of at least 70% by weight, preferably to an extent of at least 80% by weight, and may additionally comprise carbon dioxide, low boilers and traces of water. The wastewater stream h2 comprises predominantly water, generally to an extent of at least 65% by weight, and generally additionally comprises carbon dioxide. In addition, hydrocarbons (low boilers and $C_4$ hydrocarbons) may also be present.

The hydrocarbon streams h1 and, if appropriate, the stream g1 removed by phase separation are recycled partly or fully into the first dehydrogenation zone.

The offgas stream g2 generally comprises predominantly carbon dioxide and in some cases inert gases, additionally hydrogen, $C_4$ hydrocarbons to a small extent and in some cases low boilers.

The phase separation is preferably effected under gravity in a horizontal or vertical phase separator. The phase separator may comprise sedimentation aids (for example random packings or plates) or coalescent filters (for example of fiber material).

To remove the hydrogen present in the offgas stream g2, it may, if appropriate on completion of cooling, for example in an indirect heat exchanger, be passed through a membrane, generally configured as a tube, which is permeable only to molecular hydrogen. The thus removed molecular hydrogen may, if required, be used at least partly in the dehydrogenation or else sent to another utilization, for example for generating electrical energy in fuel cells.

EXAMPLE

A feed gas stream (4) comprising n-butane, said stream being obtained by combining a fresh gas stream (1) and a recycle stream (15), is fed to the first, autothermally operated, nonoxidative catalytic n-butane dehydrogenation stage (BDH) (18). To provide the heat required for the endothermic dehydrogenation, hydrogen is combusted selectively. To this end, combustion air is fed as stream (2). In order to counteract carbonization of the catalyst and prolong the lifetime of the catalyst, steam (3) is also added. A dehydrogenation gas mixture (5) is obtained, which is cooled after leaving the autothermal dehydrogenation stage (18) and fed to the second, oxidative, n-butane dehydrogenation stage (ODH) (19). Also fed to the second dehydrogenation stage (19) is an oxygen stream (6). For BDH and ODH, based on experimental results, the degrees of conversion and selectivities reproduced in Table 1 were assumed.

TABLE 1

| Reaction stage | Conversion [%] | Selectivity [%] |
|---|---|---|
| Autothermal dehydrogenation (BDH) | 49.5 (n-butane) | 97.9 (to butenes/butadiene) |
| Oxidative dehydrogenation (ODH) | 100.0 (1-butene) 92.7 (2-butene) | 95.0 (to butadiene) |

From the exit gas of the oxydehydrogenation (7), which is under a pressure of 2.2 bar, the residual oxygen is removed by catalytic combustion of hydrogen, which results in a virtually oxygen-free gas stream (7a). To this end, the gas stream (7) is contacted with a catalyst in the reactor (20). Subsequently, the gas stream (7a) is cooled and compressed to a pressure of 5.1 bar in a compressor (21) and cooled to a temperature of 55° C., to obtain a wastewater stream 8. The compressed gas (9) is cooled and fed to an extraction column (22), where the removal of butadiene (10) is effected using NMP as a solvent. The exit gas of the butadiene extraction stage (22), which is under a pressure of 5 bar and consists substantially of n-butane, carbon dioxide and hydrogen and additionally low boilers and steam, is compressed to a pressure of 30.1 bar in two stages in two compressors (23) and (24) with intermediate cooling, and the compressed gas (14) is cooled to a temperature of 5° C. in two stages in a condenser (25). The condensate (12) is obtained at a pressure of 12 bar and a temperature of 55° C.; the condensate (14a) is obtained at a pressure of 30.1 bar and a temperature of 55° C. The condensate streams (12), (14a), (17a1) and (17a2) obtained in the compression/condensation comprise predominantly n-butane and additionally carbon dioxide, water, butenes and low boilers. The uncondensed offgas (17) is hydrogen-rich and is fed either to a combustion or a material utilization (pressure-swing absorption, membrane removal of the hydrogen). The condensate streams are fed to a phase separator and separated into an aqueous phase (wastewater stream 16) and an organic phase (15).

The results of the simulation calculation are reported in Table 2. The composition of the streams (1) to (17a2) is reported in parts by weight.

TABLE 2

| | Stream No. | | | | | | | | |
|---|---|---|---|---|---|---|---|---|---|
| | 1 | 2 | 3 | 4 | 5 | 6 | 7 | 7a | 8 |
| Amount [kg/h] | 24834 | 4779 | 1231 | 59068 | 59067 | 9799 | 68866 | 68865 | 14685 |
| PROPANE | 0.0000 | 0.0000 | 0.0000 | 0.0243 | 0.0309 | 0.0000 | 0.0265 | 0.0265 | 0.0187 |
| BUTANE | 1.0000 | 0.0000 | 0.0000 | 0.8408 | 0.4272 | 0.0000 | 0.3665 | 0.3665 | 0.0001 |
| 1-BUTENE | 0.0000 | 0.0000 | 0.0000 | 0.0000 | 0.1155 | 0.0000 | 0.0000 | 0.0000 | 0.0000 |
| CIS-2-BUTENE | 0.0000 | 0.0000 | 0.0000 | 0.0032 | 0.1174 | 0.0000 | 0.0050 | 0.0050 | 0.0094 |
| TRANS-2-BUTENE | 0.0000 | 0.0000 | 0.0000 | 0.0074 | 0.1471 | 0.0000 | 0.0113 | 0.0113 | 0.0201 |
| 1,3-BUTADIENE | 0.0000 | 0.0000 | 0.0000 | 0.0000 | 0.0208 | 0.0000 | 0.3014 | 0.3014 | 0.0003 |
| WATER | 0.0000 | 0.0000 | 1.0000 | 0.0216 | 0.1059 | 0.0000 | 0.2052 | 0.2102 | 0.9419 |
| CARBON DIOXIDE | 0.0000 | 0.0000 | 0.0000 | 0.0218 | 0.0284 | 0.0000 | 0.0729 | 0.0729 | 0.0095 |
| HYDROGEN | 0.0000 | 0.0000 | 0.0000 | 0.0000 | 0.0057 | 0.0000 | 0.0049 | 0.0043 | 0.0000 |
| OXYGEN | 0.0000 | 0.9901 | 0.0000 | 0.0801 | 0.0004 | 0.9912 | 0.0046 | 0.0000 | 0.0000 |
| N2 | 0.0000 | 0.0099 | 0.0000 | 0.0008 | 0.0008 | 0.0088 | 0.0019 | 0.0019 | 0.0000 |
| Temperature [° C.] | 25 | 10 | 143.61 | 420 | 520 | 17.5 | 380 | 55 | 55 |
| Pressure [bar] | 3.2 | 3.2 | 3.2 | 3.2 | 2.7 | 2.7 | 2.2 | 2.1 | 5.1 |

| | Stream No. | | | | | | |
|---|---|---|---|---|---|---|---|
| | 9 | 10 | 11 | 12 | 13 | 14a | 14 |
| Amount [kg/h] | 54180 | 20750 | 33430 | 15971 | 17459 | 10227 | 7232 |
| PROPANE | 0.0286 | 0.0000 | 0.0463 | 0.0555 | 0.0379 | 0.0504 | 0.0203 |
| BUTANE | 0.4658 | 0.0000 | 0.7549 | 0.8675 | 0.6519 | 0.8559 | 0.3634 |
| 1-BUTENE | 0.0000 | 0.0000 | 0.0000 | 0.0000 | 0.0000 | 0.0000 | 0.0000 |
| CIS-2-BUTENE | 0.0038 | 0.0000 | 0.0062 | 0.0077 | 0.0049 | 0.0066 | 0.0024 |
| TRANS-2-BUTENE | 0.0088 | 0.0000 | 0.0143 | 0.0173 | 0.0117 | 0.0155 | 0.0062 |
| 1,3-BUTADIENE | 0.3830 | 1.0000 | 0.0000 | 0.0000 | 0.0000 | 0.0000 | 0.0000 |
| WATER | 0.0119 | 0.0000 | 0.0193 | 0.0338 | 0.0060 | 0.0079 | 0.0034 |
| CARBON DIOXIDE | 0.0901 | 0.0000 | 0.1460 | 0.0182 | 0.2629 | 0.0637 | 0.5445 |
| HYDROGEN | 0.0055 | 0.0000 | 0.0089 | 0.0000 | 0.0170 | 0.0000 | 0.0410 |
| OXYGEN | 0.0001 | 0.0000 | 0.0001 | 0.0000 | 0.0002 | 0.0000 | 0.0004 |
| N2 | 0.0025 | 0.0000 | 0.0040 | 0.0000 | 0.0076 | 0.0000 | 0.0184 |
| Temperature [° C.] | 55 | 111.66 | 111.66 | 55 | 55 | 55 | 55 |
| Pressure [bar] | 5.1 | 5 | 5 | 12 | 12 | 30.1 | 30.1 |

| | Stream No. | | | | |
|---|---|---|---|---|---|
| | 15 | 16 | 17 | 17a1 | 17a2 |
| Amount [kg/h] | 28229 | 813 | 4387 | 1834 | 1011 |
| PROPANE | 0.05080 | 0.07185 | 0.01273 | 0.03283 | 0.03015 |
| BUTANE | 0.87976 | 0.00501 | 0.09033 | 0.81808 | 0.72345 |
| 1-BUTENE | 0.00000 | 0.00000 | 0.00000 | 0.00000 | 0.00000 |
| CIS-2-BUTENE | 0.00678 | 0.01858 | 0.00046 | 0.00595 | 0.00469 |
| TRANS-2-BUTENE | 0.01556 | 0.04243 | 0.00132 | 0.01464 | 0.01212 |
| 1,3-BUTADIENE | 0.00000 | 0.00000 | 0.00000 | 0.00000 | 0.00000 |
| WATER | 0.00151 | 0.74052 | 0.00013 | 0.01031 | 0.00476 |
| CARBON DIOXIDE | 0.04559 | 0.12157 | 0.79644 | 0.11815 | 0.22475 |
| HYDROGEN | 0.00000 | 0.00001 | 0.06754 | 0.00001 | 0.00001 |
| OXYGEN | 0.00000 | 0.00000 | 0.00070 | 0.00000 | 0.00001 |
| N2 | 0.00001 | 0.00003 | 0.03035 | 0.00003 | 0.00008 |
| Temperature [° C.] | 30 | 30 | 5 | 30 | 5 |
| Pressure [bar] | 30.1 | 30.1 | 30.1 | 30.1 | 30.1 |

What is claimed is:

1. A process for preparing butadiene from n-butane, comprising the steps of
   A) providing a feed gas stream (a) comprising n-butane;
   B) feeding said feed gas stream (a) into at least one first dehydrogenation zone and nonoxidatively, catalytically dehydrogenating n-butane to obtain a gas stream (b) comprising n-butane, 1-butene, 2-butene, butadiene, and hydrogen, and optionally comprising carbon dioxide and/or steam;
   C) feeding said gas stream (b) and an oxygenous gas into at least one second dehydrogenation zone and oxidatively dehydrogenating 1-butene and 2-butene to obtain a gas stream (c) comprising n-butane, hydrogen, carbon dioxide, and steam;
   D) compressing in at least one first compression stage and cooling said gas stream (c) to obtain at least one condensate stream (d1) comprising water, and a gas stream (d2) comprising n-butane, butadiene, hydrogen, carbon dioxide, and steam;
   E) separating said gas stream (d2) by extractive distillation into a product stream (e1) consisting substantially of butadiene, and a stream (e2) comprising n-butane, hydrogen, carbon dioxide, and steam,
   F) compressing in at least one further compression stage and cooling said gas stream (e2) to obtain at least one condensate stream (f1) comprising n-butane and water, and a gas stream (f2) comprising n-butane, hydrogen, and carbon dioxide,
   G) cooling said gas stream (f2) to obtain a condensate stream (g1) comprising n-butane, and an offgas stream (g2) comprising carbon dioxide and hydrogen, and
   H) removing water from said at least one condensate stream (f1), and optionally from said condensate stream (g1), by phase separation to obtain at least one recycle stream (h1) comprising n-butane, and at least one wastewater stream (h2), and recycling said at least one recycle stream (h1) into said first dehydrogenation zone.

2. The process according to claim 1, wherein the nonoxidative, catalytic dehydrogenation of n-butane of step B) is carried out autothermally while feeding in an oxygenous gas.

3. The process according to claim 2, wherein said oxygenous gas is air.

4. The process according to claim 2, wherein said oxygenous gas is oxygen of technical-grade purity.

5. The process according to claim 1, wherein said feed stream is obtained from liquefied petroleum gas.

6. The process according to claim 1, comprising the additional step of removing the oxygen remaining in the product gas of the oxidative dehydrogenation by reacting it catalytically with hydrogen after step C).

* * * * *

UNITED STATES PATENT AND TRADEMARK OFFICE
CERTIFICATE OF CORRECTION

PATENT NO. : 7,435,860 B2
APPLICATION NO. : 11/721240
DATED : October 14, 2008
INVENTOR(S) : Sven Crone et al.

It is certified that error appears in the above-identified patent and that said Letters Patent is hereby corrected as shown below:

On the Title Page, Item (54)
    In the Title, "METHOD FOR THE PRODUCTION OF BUTADINE FROM N-BUTANE." should read -- METHOD FOR THE PRODUCTION OF BUTADIENE FROM N-BUTANE. --

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

PATENT NO.         : 7,435,860 B2
APPLICATION NO. : 11/721240
DATED               : October 14, 2008
INVENTOR(S)       : Sven Crone et al.

It is certified that error appears in the above-identified patent and that said Letters Patent is hereby corrected as shown below:

On the Title Page, Item (54) and Column 1, lines 1 and 2,
    In the Title, "METHOD FOR THE PRODUCTION OF BUTADINE FROM N-BUTANE." should read -- METHOD FOR THE PRODUCTION OF BUTADIENE FROM N-BUTANE. --

This certificate supersedes the Certificate of Correction issued December 23, 2008.

Signed and Sealed this

Twenty-seventh Day of January, 2009

JOHN DOLL
*Acting Director of the United States Patent and Trademark Office*